(12) United States Patent
Jiang et al.

(10) Patent No.: US 12,178,646 B2
(45) Date of Patent: Dec. 31, 2024

(54) MULTIFUNCTIONAL PROBE AND DETECTION METHOD THEREOF

(71) Applicant: QISDA CORPORATION, Taoyuan (TW)

(72) Inventors: Fu Sheng Jiang, Taoyuan (TW); Hsiang Wei Hsieh, Taoyuan (TW); Yi Hsiang Chan, Taoyuan (TW)

(73) Assignee: Qisda Corporation, Taoyuan (TW)

( * ) Notice: Subject to any disclaimer, the term of this patent is extended or adjusted under 35 U.S.C. 154(b) by 0 days.

(21) Appl. No.: 17/721,371

(22) Filed: Apr. 15, 2022

(65) Prior Publication Data
US 2023/0233184 A1 Jul. 27, 2023

(30) Foreign Application Priority Data
Jan. 26, 2022 (TW) .................................. 111103361

(51) Int. Cl.
*A61B 8/00* (2006.01)
*A61B 8/06* (2006.01)
*A61B 8/08* (2006.01)
*A61B 8/14* (2006.01)

(52) U.S. Cl.
CPC .............. *A61B 8/4477* (2013.01); *A61B 8/06* (2013.01); *A61B 8/14* (2013.01); *A61B 8/4488* (2013.01); *A61B 8/488* (2013.01)

(58) Field of Classification Search
CPC ........... A61B 8/4477; A61B 8/06; A61B 8/14; A61B 8/4488; A61B 8/488
See application file for complete search history.

(56) References Cited

U.S. PATENT DOCUMENTS

| | | | | |
|---|---|---|---|---|
| 2006/0241460 A1* | 10/2006 | Kimura | .............. | A61B 5/02035 600/454 |
| 2008/0034844 A1* | 2/2008 | Manneville | ............ | G01N 29/02 73/54.23 |
| 2010/0313628 A1* | 12/2010 | Kim | ...................... | G01S 7/5205 73/1.82 |
| 2013/0310691 A1* | 11/2013 | Furman | .................. | A61B 8/488 600/447 |

(Continued)

FOREIGN PATENT DOCUMENTS

| | | |
|---|---|---|
| CN | 110279938 A | 9/2019 |
| CN | 111616742 A | 9/2020 |

(Continued)

*Primary Examiner* — Amal Aly Farag (57) ABSTRACT

A multifunctional probe includes a hand-held housing, a signal detector and an array probe. The signal detector is flexibly disposed on the hand-held housing or at its first end. The array probe is disposed at one end (e.g., second end) of the hand-held housing and electrically coupled to the signal detector. The first contact time of the signal detector in contact with the living body may at least partially overlap with the second contact time of the array probe in contact with the living body. The signal detector and the array probe generate the first electronic signal. The multifunctional probe includes a flexibly-connected signal detector and an array probe, which can contact and/or detect the living body at the same time. Thus, the detection efficiency and accuracy are effectively increased. A detection method applied to the multifunctional probe is also provided.

16 Claims, 5 Drawing Sheets

(56) References Cited

U.S. PATENT DOCUMENTS

| | | | | |
|---|---|---|---|---|
| 2014/0005530 A1* | 1/2014 | Liu | ........................ | A61B 8/085 |
| | | | | 600/443 |
| 2014/0163374 A1* | 6/2014 | Ogasawara | .............. | A61B 8/02 |
| | | | | 600/443 |
| 2017/0168020 A1* | 6/2017 | Omata | .................... | G01N 29/11 |
| 2020/0375568 A1* | 12/2020 | Pagoulatos | ............ | A61B 7/008 |

FOREIGN PATENT DOCUMENTS

| | | |
|---|---|---|
| CN | 215605681 U | 1/2022 |
| TW | I620601 B | 4/2018 |

\* cited by examiner

MULTIFUNCTIONAL PROBE AND DETECTION METHOD THEREOF

FIELD OF THE INVENTION

The present invention relates to an ultrasonic detection technology, and more particularly to a multifunctional probe and a detection method thereof.

BACKGROUND OF THE INVENTION

For a general array probe, a signal emitting element first emits a signal to a target (e.g., the tissue of a living body), a signal receiving element then receives the echo signal reflected by the target, and the relative distance between the array probe and the target is calculated according to the distance measurement principle. However, because the application of the existing array probes (such as ultrasonic probes) is too limited, the existing array probe needs to be replaced with another detection probe when detecting another biological parameter of the tissue of the living body, which causes inconvenience in use.

SUMMARY OF THE INVENTION

In order to solve the shortcomings of the above technologies, the present invention provides a multifunctional probe and a detection method thereof, so as to increase the diversity of the detection of the tissue of the living body.

In a first aspect, the present invention provides a multifunctional probe, which includes:
a hand-held housing;
a signal detector and an array probe, flexibly disposed on the hand-held housing; and
an array probe, disposed at one end of the hand-held housing and electrically coupled to the signal detector, wherein a first contact time of the signal detector in contact with a living body at least partially overlaps with a second contact time of the array probe in contact with the living body, and the signal detector and the array probe are configured to generate a first electronic signal.

In another aspect, the present invention provides a detection method applied to a signal detector and an array probe of a multifunctional probe. A first contact time of the signal detector in contact with a living body at least partially overlaps with a second contact time of the array probe in contact with the living body. The detection method includes steps of:
configuring the signal detector to transmit an ultrasonic signal to a tissue in the living body; and
configuring the array probe to receive an ultrasonic echo signal reflected by the tissue.

Based on the above, the present invention provides a multifunctional probe including a hand-held housing, a signal detector and an array probe. The signal detector is flexibly disposed on the hand-held housing or at its first end. The array probe is disposed at one end (e.g., second end) of the hand-held housing and electrically coupled to the signal detector. The first contact time of the signal detector in contact with the living body may at least partially overlap with the second contact time of the array probe in contact with the living body. The signal detector and the array probe generate the first electronic signal. The multifunctional probe of the present invention includes a signal detector and an array probe, and the signal detector and the array probe can contact and/or detect the living body at the same time. Thus, the detection efficiency and accuracy of the multifunctional probe of the present invention are effectively increased. The signal detector may be, for example, a rhyometer, an electronic stethoscope, or an electrocardiogram (ECG) electrode patch. In addition, the present invention also provides a multifunctional probe, which includes a hand-held housing, a signal detector, an array probe and a biological sound monitor. The signal detector, the array probe and the biological sound monitor can contact and/or detect the living body at the same time to generate the first electronic signal. Thus, the applicability of the multifunctional probe of the present invention is effectively increased. The signal detector may be, for example, a rhyometer, and the biological sound monitor may be, for example, an electronic stethoscope or an electrocardiogram electrode patch.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
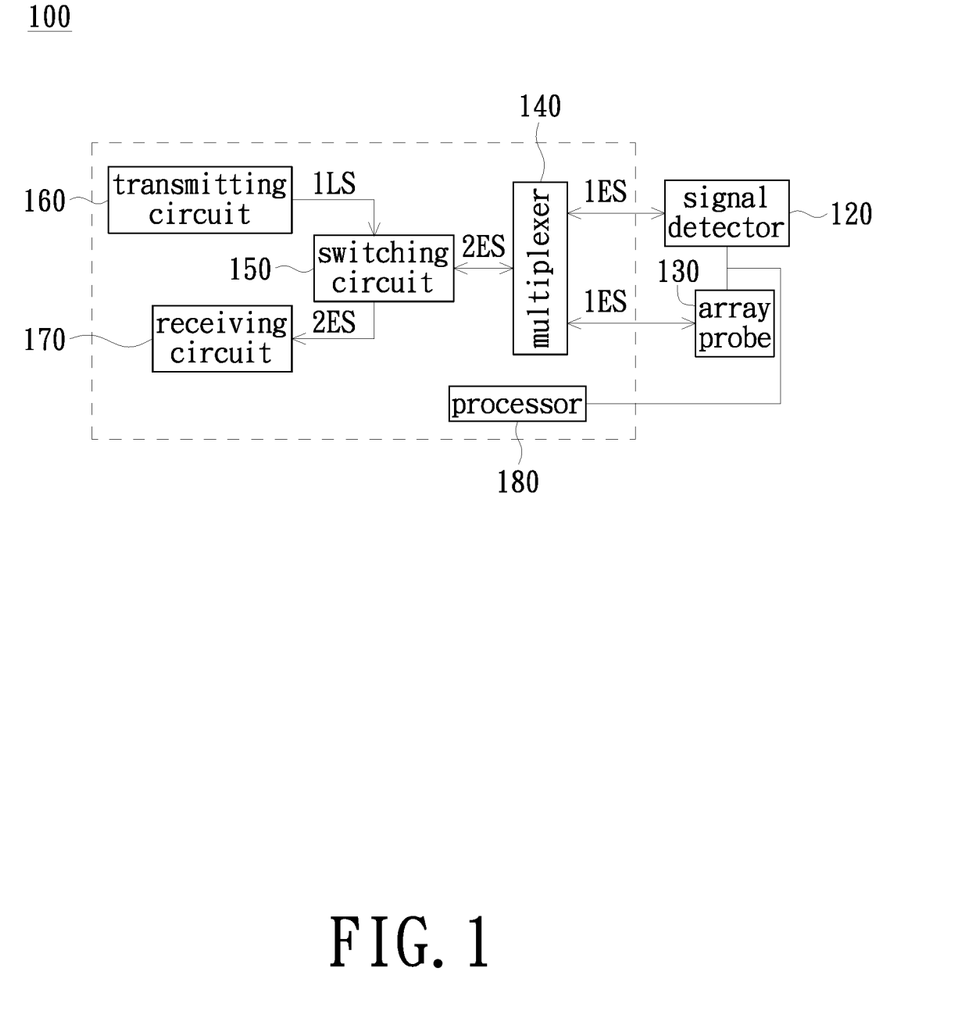
FIG. 1 is a functional block view of a multifunctional probe according to an embodiment of the present invention.
Figure 2A:
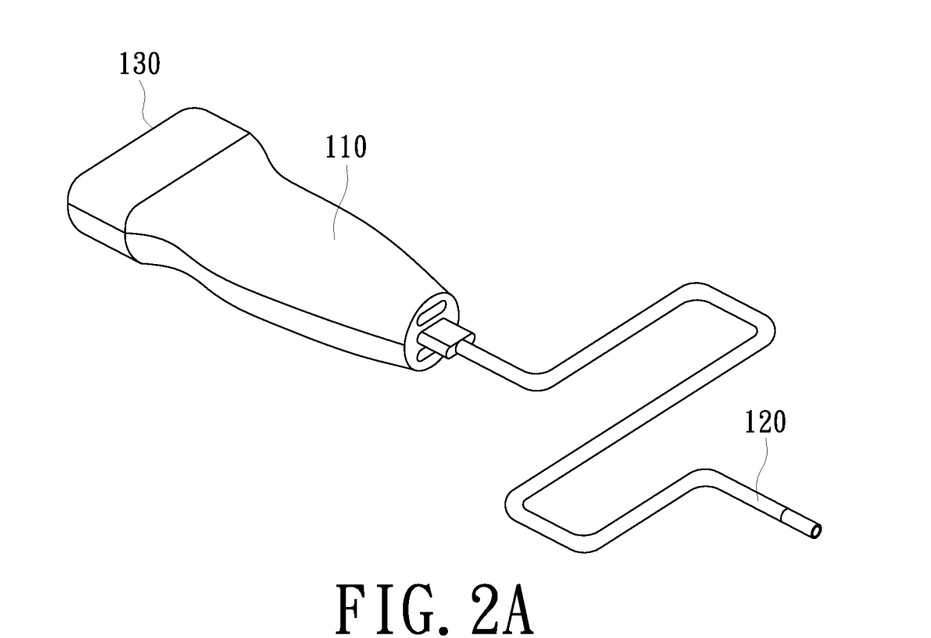
FIG. 2A is a schematic appearance view of a multifunctional probe according to an embodiment of the present invention.
Figure 2B:
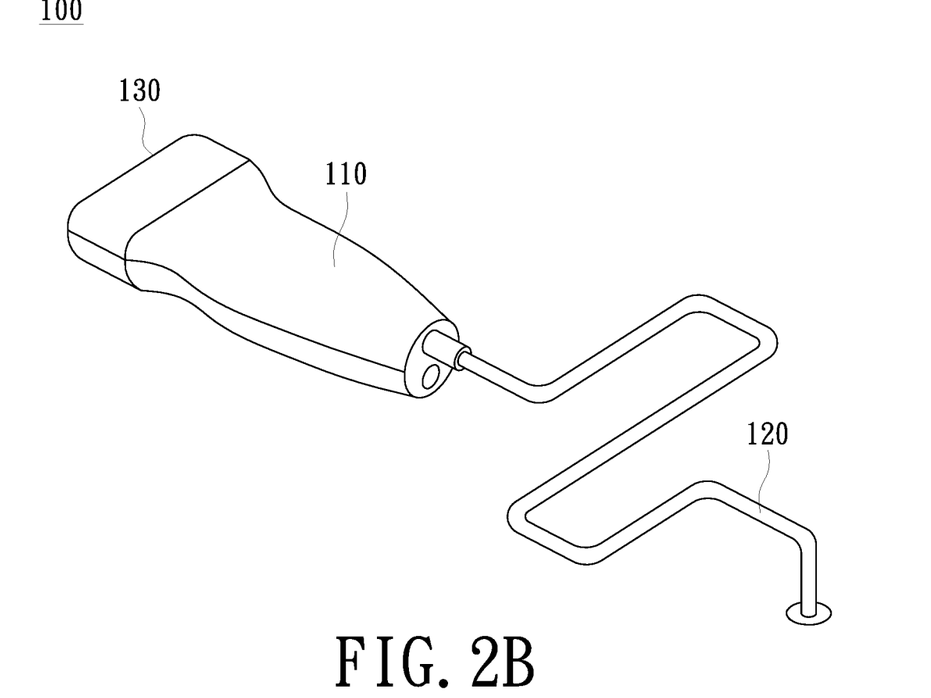
FIG. 2B is a schematic appearance view of a multifunctional probe (configured with an array probe and an electronic stethoscope/electrocardiogram (ECG) electrode patch) according to an embodiment of the present invention.
Figure 2C:
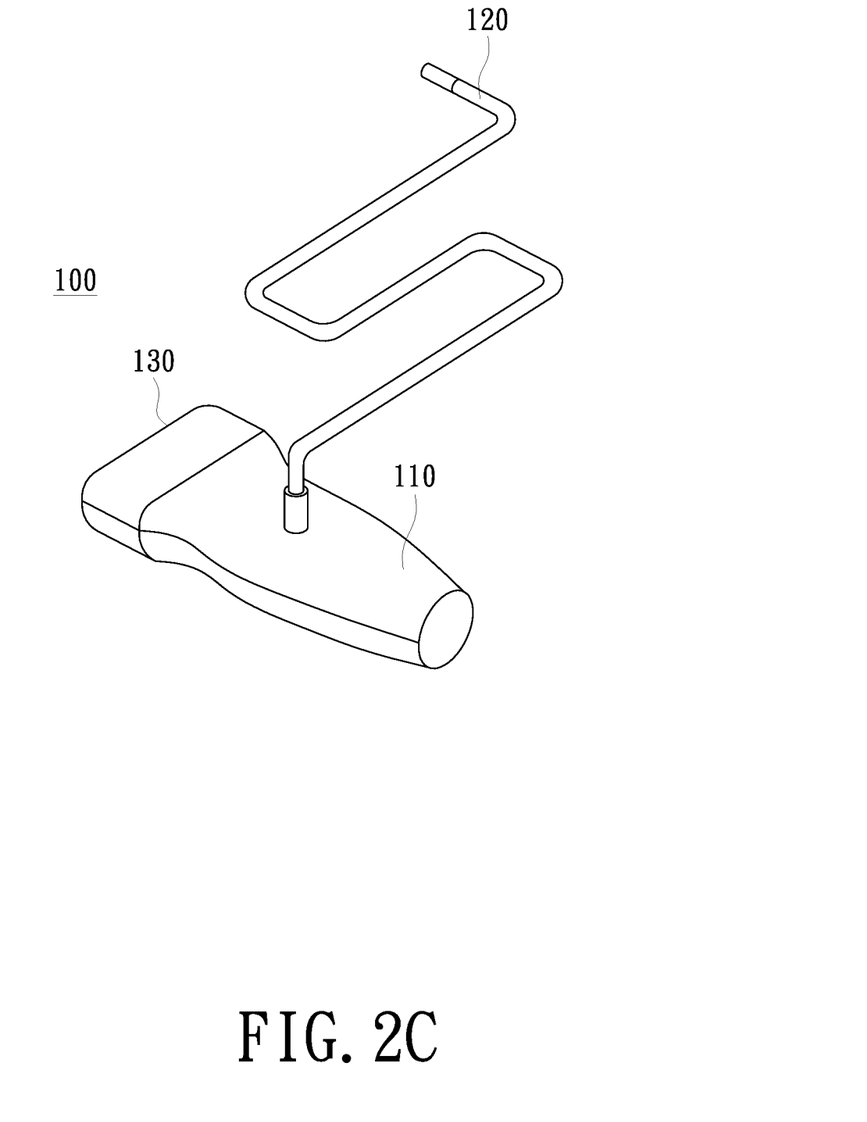
FIG. 2C is a schematic appearance view of a multifunctional probe according to another embodiment of the present invention.
Figure 3:
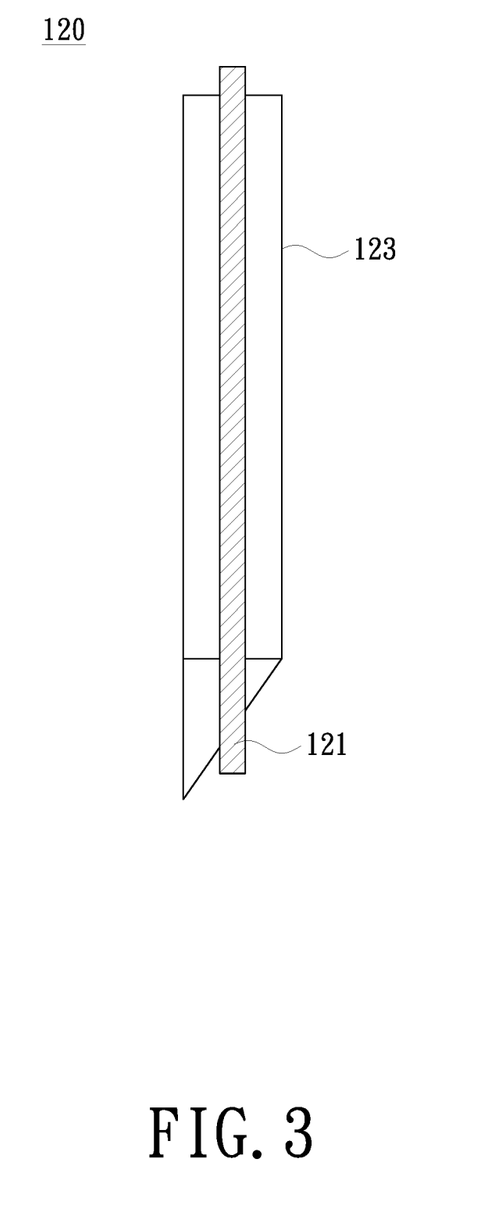
FIG. 3 is a schematic appearance view of a signal detector according to an embodiment of the present invention.

Please refer to FIGS. 1, 2A, 2B, 2C and 3 together. FIG. 1 is a functional block view of a multifunctional probe according to an embodiment of the present invention. FIG. 2A is a schematic appearance view of a multifunctional probe according to an embodiment of the present invention. FIG. 2B is a schematic appearance view of a multifunctional probe (configured with an array probe and an electronic stethoscope/electrocardiogram (ECG) electrode patch) according to an embodiment of the present invention. FIG. 2C is a schematic appearance view of a multifunctional probe according to another embodiment of the present invention. FIG. 3 is a schematic appearance view of a signal detector according to an embodiment of the present invention. The multifunctional probe 100 includes a hand-held housing 110, a signal detector 120, an array probe 130, a multiplexer 140, a switching circuit 150, a transmitting circuit 160, a receiving circuit 170 and a processor 180. The signal detector 120 is flexibly disposed on the hand-held housing 110 or at the first end of the hand-held housing 110. The array probe 130 is disposed at one end (e.g., second end) of the hand-held housing 110. Further, the array probe 130 and the signal detector 120 are, for example, respectively disposed on two opposite sides of the hand-held housing 110.

Please refer to FIGS. 2A, 2B and 2C. The signal detector 120 is fixed on the hand-held housing 110 or at its first end in a flexible configuration. In other words, the flexible configuration includes flexibility in addition to wires. Flexibility refers to the ability of an object to retain the shape before the force and deformation after the force on the object is lost. For example, when a wire is coated with a rubber material with good elasticity, the wire coated with the rubber material will deform after being stressed but the shape of the wire coated with the rubber material will return to its original shape after the stress disappears. Thus, the flexibility of the signal detector 120 is effectively increased. The signal detector 120 can be applied to one-dimensional array transducers, 1.5D transducers, two-dimensional array transducers, array transducers with more than two dimensions, linear transducers, arc transducers, circular transducers, double-curvature transducers, transducers with more than two curvatures, spherical transducers, aspherical transducers or composite transducers, wherein the aforementioned composite transducer can be an array transducer with arc and liner configuration. Users can change the type of transducer according to their needs, thus, the flexibility is effectively increased.

In one embodiment as shown in FIG. 1, the array probe 130 is electrically coupled to the signal detector 120, the multiplexer 140 is electrically coupled to the array probe 120 and the signal detector 130, the switching circuit 150 is electrically coupled to the multiplexer 140, the transmitting circuit 160 is electrically coupled to the switching circuit 150, the receiving circuit 170 is electrically coupled to the switching circuit 150, and the processor 180 is electrically coupled to the array probe 130 and the signal detector 120. Coupling includes direct coupling and indirect coupling in the field of circuits. That is, the scope of coupling includes the configuration in which no matter whether there are other elements between the two coupled electronic components. In other words, when electronic component A is coupled to electronic component C through electronic component B, it is referred that electronic component A is indirectly coupled to electronic component C, electronic component A is directly coupled to electronic component B, and electronic component B is directly coupled to electronic component C.

In one embodiment as shown in FIG. 1, the first contact time of the signal detector 120 in contact with a living body may at least partially overlap with the second contact time of the array probe 130 in contact with the living body, and the signal detector 120 and the array probe 130 generate the first electronic signal 1ES. Further, the signal detector 120 and the array probe 130 can transmit and/or receive signals to the tissue of the living body at the same time, wherein the aforementioned signals can be, for example, ultrasonic signals or ultrasonic echo signals. The multiplexer 140 at least includes the function of receiving and transmitting the first electronic signal 1ES. The signal detector 120 and the array probe 130 can convert the first electronic signal 1ES into an ultrasonic signal, or convert an ultrasound echo signal reflected by a tissue of the living body into the first electronic signal 1ES. The first electronic signal 1ES is then transmitted to the multiplexer 140. The processor 180 provides a detection result according to the first electronic signal 1ES. Specifically, the processor 180 calculates the first electronic signal 1ES according to the built-in firmware or software to obtain the detection result. The detection result includes the position, distance or depth information of at least a part of the tissue of the living body. The switching circuit 150 can switch the multifunctional probe 100 to a transmitting mode or a receiving mode. Further, the switching circuit 150 at least transmits and receives the second electronic signal 2ES. In other words, the switching circuit 150 can have two modes, the transmitting mode and the receiving mode, and the multifunction probe 100 is correspondingly in the transmitting mode or the receiving mode when the switching circuit 150 is in the transmitting mode or the receiving mode.

In one embodiment, the signal detector 120 can penetrate the superficial layer of the tissue of the living body in an invasive manner when the signal detector 120 is, for example, a rheometer. When the switching circuit 150 is in the transmitting mode, the switching circuit 150 receives the transmitting signal 1LS generated by the transmitting circuit 160, and accordingly the signal detector 120 generates an ultrasonic signal to the tissue of the living body. When the switching circuit 150 is in the receiving mode, the array probe 130 can receive the ultrasonic echo signal reflected by the tissue of the living body. Thus, through the coupled functional circuits (e.g., the multiplexer 140, the switching circuit 150, the transmitting circuit 160, the receiving circuit 170 and the processor 180), the position, distance or depth information of at least a part of the tissue of the living body is obtained, thereby effectively increasing the detection accuracy. In addition, the signal detector 120 and the array probe 130 of the present invention share a plurality of functional circuits (e.g., the multiplexer 140, the switching circuit 150, the transmitting circuit 160, the receiving circuit 170 and the processor 180) to achieve the function of detecting the position, distance or depth information of at least a part of the tissue of the living body at the same time, thereby effectively reducing the cost and volume of the circuit.

In one embodiment as shown in FIG. 1, the detection result provided by the processor 180 according to the first electronic signal 1ES includes the distance between the signal detector 120 and the tissue of the living body. Specifically, a first sound signal is generated when the distance between the signal detector 120 and the tissue is less than a preset distance value. The frequency of the first sound signal is negatively correlated with the distance between the signal detector 120 and the tissue. For example, when the signal detector 120 is too close to a target (e.g., a specific tissue), the first sound signal generates a warning sound like a reversing radar, that is, the distance between the signal detector 120 and the tissue is inversely proportional to the sound frequency (e.g., the smaller the distance, the higher the sound frequency).

In one embodiment as shown in FIG. 2B, the signal detector 120 may be a biological sound monitor, wherein the first electronic signal 1ES is a second sound signal or an electronic sound signal. The aforementioned biological sound monitor includes an electronic stethoscope or an electrocardiogram electrode patch. Electrocardiogram electrode patch is a diagnosis and treatment technology in which the electrophysiological activity of the heart is captured and recorded through the body wall in units of time by the electrodes in contact with the skin. The multifunctional probe 100 of the present invention includes a signal detector 120 and an array probe 130 on the hand-held housing 110 or at the two ends thereof at the same time, which effectively increases the applicability.

In one embodiment as shown in FIGS. 2A, 2B, 2C and 3, the signal detector 120 and the array probe 130 are detachable. The signal detector 120 can be a rheometer 121, an electronic stethoscope or an electrocardiogram electrode patch. The array probe 130 can be can an one-dimensional array transducer, a 1.5D transducer, a two-dimensional array transducer, an array transducer with more than two dimensions, a linear transducer, an arc transducer, a circular transducer, a double-curvature transducer, a transducer with more than two curvatures, a spherical transducer, an aspherical transducer or a composite transducer, wherein the aforementioned composite transducer can be an array transducer with arc and liner configuration. The rheometer 121 may be, for example, a measuring instrument (e.g., Transonic HT 300 model) designed for various surgeries and configured to measure and monitor the blood flow of various blood vessels, including arteries, veins, and catheters used during surgery. Therefore, the blood flow of the blood vessel or organ during the surgery can be accurately assessed. In one embodiment the quantitative data (ml/min) of the blood vessel can be seen on the instrument as long as the measuring probe is hooked on the blood vessel to be measured. In another embodiment in which an external pipeline measurement sensor is used, the flow rate of the liquid flowing in the pipeline can be clearly observed when the sensor is clamped on the pipeline. The position of the signal detector 120 is not limited to a specific position on the hand-held housing 110. That is, the signal detector 120 can be disposed anywhere on the hand-held housing 110 in another embodiment, as shown in FIG. 2C.

In one embodiment as shown FIG. 3, the rheometer 121 is coated with a casing needle 123. The casing needle 123 can fix the position of the rheometer 121. The rheometer 121 can obtain an A-mode signal (waveform) and a blood flow signal (waveform). The A-mode signal and the blood flow signal are converted into a first sound signal or a displayed numerical value, so as to remind the user of the proximity or distance between the needle of the rheometer 121 and the target. An ultrasonic probe is used to detect specific human tissues, such as nerves, adipose tissues, etc, due to each tissue has its different frequency characteristic. Thus, the rheometer 121 can use the Doppler Effect to obtain the blood flow characteristics. Specifically, the rheometer 121 generates an ultrasonic signal, and the array probe 130 receives the ultrasonic echo signal. The processor 180 of the multifunctional probe 100 can determine whether the heart is beating through the electrocardiogram according to the ultrasonic signal generated by the rheometer 121 and the ultrasonic echo signal received by the array probe 130, especially when the pulse cannot be felt. The array probe 130 can be used to determine whether there is pericardial effusion on the structure through imaging, focusing on the pericardium with high echo in the outer circle and the diameter of the aortic root to determine whether there is significant enlargement (e.g., reverse blood flow or resistance).

In one embodiment, the first electronic signal 1ES includes at least one of an A-mode signal, a B-mode image signal, and a blood flow signal. The A-mode signal is a simple ultrasonic type signal. Specifically, the A-mode signal can be obtained by configuring a single sensor to scan a line through the living body and plotting the echoes as a function of depth on the screen. Therapeutic ultrasound for specific tumors or stones is also an A-mode signal, which can precisely locate the destructive wave energy. The B-mode image ultrasound signal can be obtained by configuring the signal detector 120 to scan the plane passing through the living body at the same time through a linear array of transducers, and a two-dimensional image can be seen on the screen. Thus, the applicability of the multifunctional probe 100 is effectively increased. For example, the array probe 130 can be used to obtain a B-mode image to know the preliminary relevant position of the affected par; then, by inserting the casing needle 123 into the superficial layer of the tissue of the living body, the rheometer 121 (e.g., yellow) in the casing needle 123 can be used to obtain waveform signals such as medical imaging information related to blood vessels and nerve tissue; and the signal detector 120 can be used to measure and display blood flow by the Doppler Effect, which can be used to assess whether structures (such as blood) are moving toward or away from the probe and the relative velocity of blood and blood vessels. For another example, the array probe 130 is used to obtain a B-mode image to know the preliminary relative position of the affected part; then, by inserting the casing needle 123 into the superficial layer of the tissue of the living body and configuring the rheometer 121 in the casing needle 123 to transmit an ultrasound signal, the array probe 130 can receive the ultrasound echo signal reflected from the ultrasound signal to precisely know the relative position of the casing needle 123 and the rheometer 121 in the B-mode image.

In the above embodiments, it should be noted that the descriptions of the multiplexer 140, the switching circuit 150, the transmitting circuit 160, the receiving circuit 170 and the processor 180 do not limit the technical scope of the present invention. That is, in practice, the multiplexer 140, the switching circuit 150, the transmitting circuit 160, the receiving circuit 170 and the processor 180 can be any configuration as long as it is realized that the first contact time of the signal detector 120 in contact with the living body at least partially overlaps with the second contact time of the array probe 130 in contact with the living body, and the signal detector 120 and the array probe 130 generate the first electronic signal. Thus, the present invention can be summarized as: a multifunctional probe 100 includes a hand-held housing 110, a signal detector 120 and an array probe 130, the signal detector 120 is flexibly disposed on the hand-held housing 110 or at its first end, the array probe 130 is disposed at one end (e.g., second end) of the hand-held housing 110, the array probe 130 is electrically coupled to the signal detector 120, the first contact time of the signal detector 120 in contact with the living body at least partially overlaps with the second contact time of the array probe 130 in contact with the living body, and the signal detector 120 and the array probe 130 generate the first electronic signal and send and/or receive signals to the tissue of the living body at the same time. Thus, the detection efficiency and accuracy of the multifunctional probe 100 of the invention are effectively increased.

Figure 4:
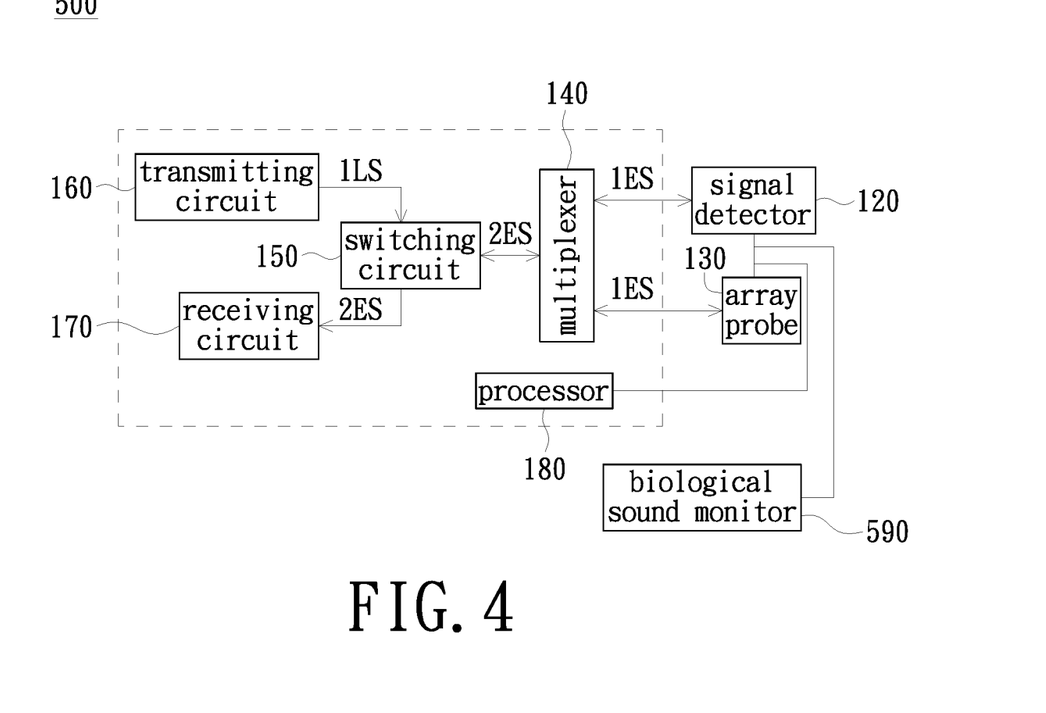
FIG. 4 is a schematic block view of a multifunctional probe according to another embodiment of the present invention.
Figure 5:
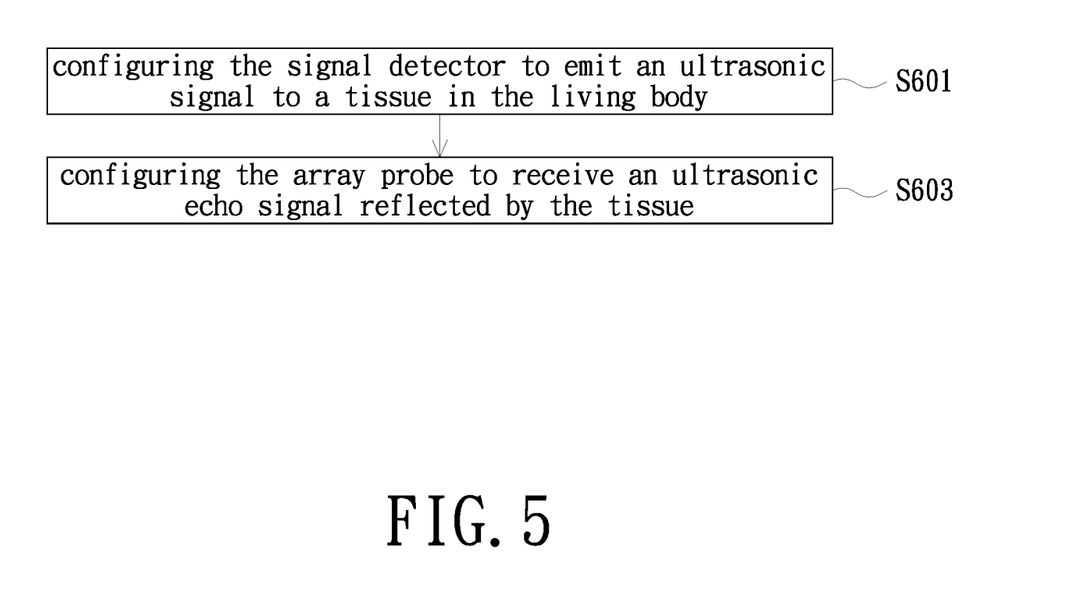
FIG. 5 is a schematic flowchart of a detection method according to an embodiment of the present invention.

FIG. 4 is a schematic block view of a multifunctional probe according to another embodiment of the present invention. Please refer to FIGS. 1 and 4 together. The multifunctional probe 500 includes a hand-held housing, a signal detector 120, an array probe 130, a multiplexer 140, a switching circuit 150, a transmitting circuit 160, a receiving circuit 170, a processor 180 and a biological sound monitor 590. The signal detector 120 is flexibly disposed on the hand-held housing or its first end, the array probe 130 is disposed on one end (e.g., second end) of the hand-held housing, and the array probe 130 is electrically coupled to the signal detector 120. The biological sound monitor 590 is disposed on the hand-held housing and electrically coupled to the signal detector 120 and the array probe 130. The third contact time of the biological sound monitor 590 in contact with the living body may at least partially overlap with the first contact time of the signal detector 120 in contact with the living body and the second contact time of the array probe 130 in contact with the living body. The signal detector 120, the array probe 130 and the biological sound monitor 590 generate the first electronic signal 1ES. Further, the signal detector 120, the array probe 130 and the biological sound monitor 590 can transmit and/or receive a signal to the tissue of the living body at the same time. The biological sound monitor 590 includes, for example, an electronic stethoscope or an electrocardiogram electrode patch. Electrocardiogram electrode patch is a diagnosis and treatment technology in which the electrophysiological activity of the heart is captured and recorded through the body wall in units of time by the electrodes in contact with the skin. The electrophysiological activity of the heart recorded by the multifunctional probe 500 can be converted into an electrocardiogram. Other related technical features are described in the embodiment of FIG. 1, and no redundant detail is to be given herein.

Please refer to FIGS. 1 to 5 together. The present invention provides a detection method applied to the signal detector 120 and the array probe 130 of the multifunctional probe 100 or 500, wherein the first contact time of the signal detector 120 in contact with the living body at least partially overlaps with the second contact time of the array probe 130 in contact with the living body. A first contact time of the signal detector 120 in contact with an object may at least partially overlap the array. A second contact time for the probe 130 to contact the organism. The detection method includes steps of: configuring the signal detector 120 to emit an ultrasonic signal to a tissue in the living body (step S601); and configuring the array probe 130 to receive an ultrasonic echo signal reflected by the tissue (step S603).

The detection method provided in the present invention is limited to the description of the detection stage, not the subsequent steps of evaluating symptoms and determining the etiology or lesion status. For the multifunctional probe 500 shown in FIG. 5, it should be noted that the step S601 of the detection method may be changed to: configuring at least one of the signal detector 120 and the biological sound monitor 590 to emit an ultrasonic signal to a tissue in the living body. That is, the signal detector 120 emits the ultrasonic signal, or the biological sound monitor 590 emits the ultrasonic signal, or the signal detector 120 and the biological sound monitor 590 together emit the ultrasonic signal, and no redundant detail is to be given herein.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A multifunctional probe, comprising:
   a hand-held housing;
   a signal detector, flexibly disposed on the hand-held housing;
   an array probe, disposed at one end of the hand-held housing and electrically coupled to the signal detector, wherein a first contact time of the signal detector in contact with a target at least partially overlaps with a second contact time of the array probe in contact with the target, and the signal detector and the array probe are configured to generate a first electronic signal;
   a multiplexer, electrically coupled to the array probe and the signal detector, wherein the multiplexer is configured to at least receive and transmit the first electronic signal;
   a switching circuit, electrically coupled to the multiplexer, wherein the switching circuit is configured to switch the multifunctional probe to a transmitting mode or a receiving mode and at least transmit and receive a second electronic signal; and
   a transmitting circuit, electrically coupled to the switching circuit, wherein the switching circuit receives a transmitting signal generated by the transmitting circuit when the switching circuit is in the transmitting mode, so that the signal detector and the array probe generate an ultrasonic signal;
   wherein the signal detector is configured to transmit a signal to the target and the array probe is configured to receive a signal from the target at the same time by partially overlapping the first contact time with the second contact time.

2. The multifunctional probe according to claim 1, further comprising:
   a receiving circuit, electrically coupled to the switching circuit, wherein the receiving circuit is configured to receive the second electronic signal through the switching circuit when the switching circuit is in the receiving mode.

3. The multifunctional probe according to claim 1, further comprising:
   a processor, electrically coupled to the array probe and the signal detector, wherein the processor is configured to provides a detection result according to the first electronic signal.

4. The multifunctional probe according to claim 3, wherein the detection result comprises a distance between the signal detector and the target, a first sound signal is generated when the distance is less than a preset distance value, and a frequency of the first sound signal is negatively correlated with the distance between the signal detector and the target.

5. The multifunctional probe according to claim 1, wherein the signal detector is a biological sound monitor, and the first electronic signal is a second sound signal or an electronic sound signal.

6. The multifunctional probe according to claim 1, wherein the signal detector and the array probe are detachable.

7. The multifunctional probe according to claim 1, wherein the signal detector is a rheometer.

8. The multifunctional probe according to claim 7, wherein the rheometer is wrapped with a casing needle.

9. The multifunctional probe according to claim 7, wherein the rheometer is configured to generate an ultrasonic signal from the target, and the array probe is further configured to receive an ultrasonic echo signal from the target, and the ultrasonic echo signal is corresponding to the ultrasonic signal.

10. The multifunctional probe according to claim 1, wherein the first electronic signal comprises at least one of an A-mode signal, a B-mode image signal and a blood flow signal.

11. The multifunctional probe according to claim 1, further comprising a biological sound monitor disposed on the hand-held housing and electrically coupled to the signal detector and the array probe, wherein a third contact time of the biological sound monitor in contact with the target at least partially overlaps with the first contact time and the second contact time, and the signal detector, the array probe and the biological sound monitor generate the first electronic signal.

12. The multifunctional probe according to claim 11, wherein the signal detector, the array probe and the biological sound monitor are further configured to transmit and/or receive a signal to the target at the same time.

13. The multifunctional probe according to claim 11, wherein the signal detector is a rheometer, and the biological sound monitor is an electronic stethoscope or an electrocardiogram electrode patch.

14. The multifunctional probe according to claim 1, wherein the signal detector is flexibly disposed at a first end of the hand-held housing, the array probe is disposed at a second end of the hand-held housing, and the first end is opposite to the second end.

15. The multifunctional probe according to claim 14, wherein the signal detector is a rheometer or a biological sound monitor.

16. A detection method applied to a signal detector, a multiplexer, a switching circuit, a transmitting circuit and an array probe of a multifunctional probe, a first contact time of the signal detector in contact with a target at least partially overlapping with a second contact time of the array probe in contact with the target, and the detection method comprising steps of:
- configuring the signal detector to transmit an ultrasonic signal to the target; and
- configuring the array probe to receive an ultrasonic echo signal reflected by the target;
- wherein the signal detector and the array probe generate a first electronic signal;
- wherein the multiplexer at least receives and transmits the first electronic signal;
- wherein the switching circuit switches the multifunctional probe to a transmitting mode or a receiving mode and at least transmits and receives a second electronic signal;
- wherein the switching circuit receives a transmitting signal generated by the transmitting circuit when the switching circuit is in the transmitting mode, so that the signal detector and the array probe generate the ultrasonic signal;
- wherein the signal detector is configured to transmit a signal to the target and the array probe is configured to receive a signal from the target at the same time by partially overlapping the first contact time with the second contact time.

* * * * *